United States Patent
Ressel et al.

(10) Patent No.: US 10,196,410 B2
(45) Date of Patent: Feb. 5, 2019

(54) PROCESS FOR PRODUCING PHOSPHORUS-CONTAINING CYANOHYDRIN ESTERS

(71) Applicant: BAYER CROPSCIENCE AKTIENGESELLSCHAFT, Monheim am Rhein (DE)

(72) Inventors: Hans-Joachim Ressel, Hattersheim (DE); Kilian Tellmann, Köln (DE); Mark James Ford, Wiesbaden-Breckenheim (DE); Martin Littmann, Leverkusen (DE); Günter Schlegel, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/756,174

(22) PCT Filed: Aug. 29, 2016

(86) PCT No.: PCT/EP2016/070305
§ 371 (c)(1),
(2) Date: Feb. 28, 2018

(87) PCT Pub. No.: WO2017/037012
PCT Pub. Date: Mar. 9, 2017

(65) Prior Publication Data
US 2018/0244702 A1    Aug. 30, 2018

(30) Foreign Application Priority Data
Sep. 2, 2015 (EP) .................... 15183424

(51) Int. Cl.
*C07F 9/32* (2006.01)
*A01N 57/18* (2006.01)

(52) U.S. Cl.
CPC ............ *C07F 9/3211* (2013.01); *A01N 57/18* (2013.01)

(58) Field of Classification Search
CPC .............................. C07F 9/3211; A01N 57/18
USPC ........................................................... 568/14
See application file for complete search history.

(56) References Cited

U.S. PATENT DOCUMENTS

| | | | |
|---|---|---|---|
| 3,914,345 A | 10/1975 | Kleiner et al. | |
| 4,168,963 A | 9/1979 | Rupp et al. | |
| 4,474,711 A | 10/1984 | Kleiner et al. | |
| 4,485,052 A | 11/1984 | Kleiner et al. | |
| 4,521,348 A * | 6/1985 | Finke | C07F 9/301 558/137 |
| 4,521,349 A | 6/1985 | Weber et al. | |
| 4,599,207 A | 7/1986 | Lachhein et al. | |
| 4,839,105 A | 6/1989 | Kleiner | |
| 5,128,495 A | 7/1992 | Scheffel et al. | |
| 6,359,162 B1 | 3/2002 | Willms | |

FOREIGN PATENT DOCUMENTS

| | | |
|---|---|---|
| EP | 0 011 245 A1 | 5/1980 |
| EP | 0 019 750 A1 | 12/1980 |

OTHER PUBLICATIONS

International Search Report of International Patent Application No. PCT/EP2016/070305 dated Oct. 4, 2016.

* cited by examiner

*Primary Examiner* — Deborah D Carr
(74) *Attorney, Agent, or Firm* — McBee Moore Woodward & Vanik IP, LLC

(57) ABSTRACT

The present invention primarily relates to a process for producing certain phosphorus-containing cyanohydrin esters of formula (I) and the use thereof for producing glufosinate/glufosinate salts. The present invention further relates to a process for producing glufosinate/glufosinate salts.

15 Claims, No Drawings

PROCESS FOR PRODUCING PHOSPHORUS-CONTAINING CYANOHYDRIN ESTERS

CROSS-REFERENCE TO RELATED APPLICATIONS

This application is a National Stage entry of International Application No. PCT/EP2016/070305, filed 29 Aug. 2016, which claims priority to European Patent Application No. 15183424.9, filed 2 Sep. 2015.

BACKGROUND

Field

The present invention primarily relates to a process for producing certain phosphorus-containing cyanohydrin esters of hereinbelow-defined formula (I) and the use thereof for producing glufosinate/glufosinate salts. The present invention further relates to a process for producing glufosinate/glufosinate salts.

Description of Related Art

Phosphorus-containing cyanohydrin esters are valuable intermediates in various industrial fields, in particular for producing biologically active substances which can be employed in the pharmaceutical/agrochemical sector.

U.S. Pat. No. 4,168,963 describes a wide variety of phosphorus-containing herbicidally active compounds, among which in particular phosphinothricin (2-amino-4-[hydroxy(methyl)phosphinoyl]butanoic acid; common name: glufosinate, referred to hereinbelow as glufosinate) and the salts thereof have attained commercial importance in the agrochemical sector.

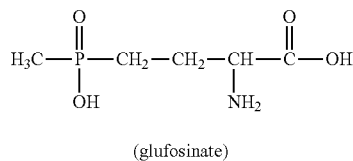

(glufosinate)

Methods for producing intermediates for the synthesis of such phosphorus-containing herbicidally active compounds, in particular of glufosinate, are described in U.S. Pat. Nos. 4,521,348, 4,599,207 and 6,359,162B1 for example.

Reactions of cyanohydrin esters and methanephosphonous esters are described in U.S. Pat. Nos. 4,521,348 or 4,599,207 for example.

While the prior art processes for producing phosphorus-containing cyanohydrin esters allow production of the desired phosphorus-containing cyanohydrin esters, in some cases in very good yield, they do still have disadvantages such as, for example, yields of phosphorus-containing cyanohydrin esters that are still in need of improvement, an excessively high proportion of coupling products or byproducts, excessively complex purification/isolation of the phosphorus-containing cyanohydrin esters and/or reaction conditions that are excessively arduous in terms of process/plant engineering.

SUMMARY

It is accordingly an object of the present invention to find a process for producing phosphorus-containing cyanohydrin esters which provides the phosphorus-containing cyanohydrin esters in further improved yield and/or results in a lower proportion of coupling products or byproducts and in addition preferably allows for an improved reaction regime, for example in terms of aspects relevant to safety, the environment and/or quality.

The hereinbelow-described process according to the invention achieves this object.

The present invention provides a process for producing phosphorus-containing cyanohydrin esters of formula (I)

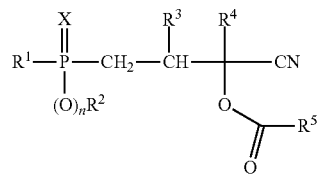

characterized in that a compound of formula (II)

is reacted with a compound of formula (III)

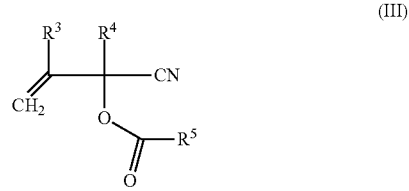

wherein in each case:

$R^1$ represents $(C_1-C_{12})$-alkyl, $(C_1-C_{12})$-haloalkyl, $(C_6-C_{10})$-aryl, $(C_6-C_{10})$-haloaryl, $(C_7-C_{10})$-aralkyl, $(C_7-C_{10})$-haloaralkyl, $(C_4-C_{10})$-cycloalkyl or $(C_4-C_{10})$-halocycloalkyl, $R^2$ represents $(C_1-C_{12})$-alkyl, $(C_1-C_{12})$-haloalkyl, $(C_6-C_{10})$-aryl, $(C_6-C_{10})$-haloaryl, $(C_7-C_{10})$-aralkyl, $(C_7-C_{10})$-haloaralkyl, $(C_4-C_{10})$-cycloalkyl or $(C_4-C_{10})$-halocycloalkyl, $R^3$ and $R^4$ each independently of one another represent hydrogen, $(C_1-C_4)$-alkyl, phenyl or benzyl, $R^5$ represents $(C_1-C_{12})$-alkyl, $(C_1-C_{12})$-haloalkyl, $(C_6-C_{10})$-aryl, $(C_6-C_{10})$-haloaryl, $(C_7-C_{10})$-aralkyl, $(C_7-C_{10})$-haloaralkyl, $(C_4-C_{10})$-cycloalkyl or $(C_4-C_{10})$-halocycloalkyl, X represents oxygen or sulphur and n is 0 or 1, in the presence of one or more free-radical-forming substances (IV) in a reactor with mixing, wherein the mixing is effected under the following parameters:

the specific power input is at least 0.03 kW/m³ (and by preference not more than 100 000 kW/m³, preferably not more than 10 000 kW/m³, more preferably not more than 5000 kW/m³), and/or the mixing time to achieve a coefficient of variation of 0.01 or lower (CoV≤10⁻²) is less than 10 seconds.

DETAILED DESCRIPTION OF A PREFERRED EMBODIMENT

The process according to the invention, particularly in one of the embodiments of the process according to the invention described as preferable/particularly preferable, affords the phosphorus-containing cyanohydrin esters of formula (I)/of hereinbelow-defined formulae (Ia)/(Ib) in improved yield and regularly in higher purity.

Overall, the processes according to the invention, and also the further hereinbelow-described process according to the invention for producing glufosinate, form fewer undesired secondary components so that the processes according to the invention are more efficient and more energy-saving.

The specific power input recited in the context of the present invention relates to the total volume of the condensed phase under the reaction conditions (i.e. the liquid and/or solid phase but not the gaseous phase) in the reactor. The specific power input in the context of the present invention thus relates not to the volume of the commixed zone(s) in the reactor but to the total volume of the condensed phase in the reactor.

The coefficient of variation CoV characterizes the distribution of the individual components in a mixture with reference to concentration differences. A coefficient of variation (CoV) of 0 stands for an ideal, completely homogeneous mixture while a coefficient of variation (CoV) of 1 stands for no commixing.

The coefficient of mixing represents the counterpart to the coefficient of variation. A coefficient of mixing of 1 stands for an ideal, completely homogeneous mixture while a coefficient of variation (CoV) of 0 stands for no commixing (cf. for example "Chemietechnik", Eckhard Ignatowitz, 8th edition (2007), page 314).

The mixing in connection with a process according to the invention may be effected according to methods known to those skilled in the art, preferably by stirring, pumped circulation or pumping through static mixers, such as, for example, static mixers (Sulzer SMX, EMB cascade mixers etc.), it additionally being possible to employ baffles.

It is preferable when in the process according to the invention the mixing is effected under the following parameters:

the specific power input is at least 0.3 kW/m$^3$ (by preference not more than 10 000 kW/m$^3$, preferably not more than 5000 kW/m$^3$, more preferably not more than 3000 kW/m$^3$ and particularly preferably not more than 1000 kW/m$^3$)

and/or the mixing time to achieve a coefficient of variation of 0.01 or lower (CoV≤10$^{-2}$) is less than 1 second.

It is preferable when in the process according to the invention the mixing is effected under the following parameters:

the specific power input is at least 3 kW/m$^3$ (and preferably not more than 5000 kW/m$^3$, more preferably not more than 3000 kW/m$^3$ and particularly preferably not more than 1000 kW/m$^3$), and/or the mixing time to achieve a coefficient of variation of 0.01 or lower (CoV≤10$^{-2}$) is less than 0.1 seconds.

The mixing is preferably effected in compliance with both parameters, i.e. the respective hereinabove-defined specific power input and, simultaneously, the respective hereinabove-defined mixing time.

In a process according to the invention the average hydrodynamic residence time in the reactor is by preference in the range from 1 to 8 hours, preferably in the range from 2 to 6 hours and particularly preferably in the range from 2.5 to 5 hours.

The process according to the invention is particularly suitable for performance on an industrial scale. The reactor volume is thus by preference at least 100 liters, preferably at least 200 liters, yet more preferably at least 250 liters.

The reactor volume is by preference not more than 250 m$^3$, preferably not more than 100 m$^3$, more preferably not more than 50 m$^3$.

The respective alkyl radicals of the radicals $R^1$, $R^2$, $R^3$, $R^4$ and $R^5$ may have a straight-chain or branched-chain (branched) carbon skeleton.

The expression "($C_1$-$C_4$)-alkyl" is a brief notation for an alkyl radical having 1 to 4 carbon atoms, i.e. encompasses the radicals methyl, ethyl, 1-propyl, 2-propyl, 1-butyl, 2-butyl, 2-methylpropyl or tert-butyl. General alkyl radicals having a larger specified range of carbon atoms, for example "($C_1$-$C_6$)-alkyl", correspondingly also encompass straight-chain or branched alkyl radicals having a greater number of carbon atoms, i.e. in this example also the alkyl radicals having 5 and 6 carbon atoms.

"Halogen" preferably refers to the group consisting of fluorine, chlorine, bromine and iodine. Haloalkyl, haloaryl, haloaralkyl and halocycloalkyl respectively refer to alkyl, aryl, aralkyl and cycloalkyl partially or completely substituted by identical or different halogen atoms, preferably from the group fluorine, chlorine and bromine, in particular from the group fluorine and chlorine. Thus haloalkyl encompasses for example monohaloalkyl (=monohalogenalkyl), dihaloalkyl (=dihalogenalkyl), trihaloalkyl (=trihalogenalkyl) or else perhaloalkyl, for example $CF_3 8$, $CHF_2$, $CH_2F$, $CF_3CF_2$, $CH_2FCHCl$, $CCl_3$, $CHCl_2$, $CH_2CH_2Cl$. The same applies for the other halogen-substituted radicals.

Suitable and preferred compounds of formula (II) include inter alia: methanephosphonous acid mono($C_1$-$C_6$)-alkyl esters, monododecyl methanephosphonate, monophenyl methanephosphonate; ethanephosphonous acid mono($C_1$-$C_6$)-alkyl esters, monododecyl ethanephosphonate, monophenyl ethanephosphonate; propanephosphonous acid mono($C_1$-$C_6$)-alkyl esters, monododecyl propanephosphonate, monophenyl propanephosphonate; butanephosphonous acid mono($C_1$-$C_6$)-alkyl esters, monododecyl butanephosphonate, monophenyl butanephosphonate; phenylphosphonous acid mono($C_1$-$C_6$)-alkyl esters, monododecyl phenylphosphonate, monophenyl phenylphosphonate; benzylphosphonous acid mono($C_1$-$C_6$)-alkyl esters, monododecyl benzylphosphonate, monophenyl benzylphosphonate; methylthiophosphonous acid mono($C_1$-$C_6$)-alkyl esters, monododecyl methylthiophosphonate, monophenyl methylthiophosphonate; dimethylphosphine oxide, diethylphosphine oxide, dipropylphosphine oxide, dibutylphosphine oxide, diphenylphosphine oxide, methylphenylphosphine oxide, dibenzylphosphine oxide, dimethylphosphine sulphide and diphenylphosphine sulphide.

The production of the compounds of formula (II) is known to those skilled in the art and may be effected according to processes known from the literature (for example U.S. Pat. Nos. 3,914,345; 4,474,711; 4,485,052; 4,839,105; 5,128,495).

The production of the cyanohydrin esters of formula (III) is likewise known to those skilled in the art and may be effected according to processes known from the literature (for example as per EP 0 019 750 A1 and as per U.S. Pat. No. 4,521,348 and the relevant documents cited therein).

It is preferable when in the process according to the invention:

$R^3$ and $R^4$ each independently of one another represent hydrogen or methyl,
and/or
X represents oxygen,
and/or
n is 1.

The process according to the invention preferably relates to the production of phosphorus-containing cyanohydrin esters of formula (Ia)

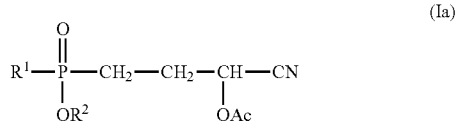

(Ia)

characterized in that a compound of formula (IIa)

(IIa)

is reacted with an acrolein cyanohydrin ester of formula (IIIa), wherein one of the compounds or the compound of formula (III) corresponds to formula (IIIa) (acrolein cyanohydrin-O-acetate, Ac=acetyl, $R^5$ in formula (I) correspondingly=methyl)

(IIIa)

wherein in each case:
$R^1$ represents $(C_1-C_6)$-alkyl, $(C_1-C_6)$-haloalkyl, $(C_6-C_8)$-aryl, $(C_6-C_8)$-haloaryl, $(C_7-C_{10})$-aralkyl, $(C_7-C_{10})$-haloaralkyl, $(C_5-C_8)$-cycloalkyl or $(C_5-C_8)$-halocycloalkyl
and
$R^2$ represents $(C_1-C_6)$-alkyl, $(C_1-C_6)$-haloalkyl, $(C_6-C_8)$-aryl, $(C_6-C_8)$-haloaryl, $(C_7-C_{10})$-aralkyl, $(C_7-C_{10})$-haloaralkyl, $(C_5-C_8)$-cycloalkyl or $(C_5-C_8)$-halocycloalkyl.

It is preferable when in each case:
$R^1$ represents $(C_1-C_4)$-alkyl or $(C_1-C_4)$-haloalkyl, preferably methyl or ethyl,
$R^2$ represents $(C_1-C_6)$-alkyl or $(C_1-C_6)$-haloalkyl, preferably $(C_3-C_6)$-alkyl, preference among these in turn being given to $C_4$-alkyl or $C_5$-alkyl.

In the process according to the invention, in formula (I)/in formula (Ia)
$R^1$ particularly preferably represents methyl and
$R^2$ particularly preferably represents $(C_1-C_6)$-alkyl, preference in turn being given to $(C_4C_5)$-alkyl.

The implementations which follow and the embodiments of the process according to the invention characterized as preferable/particularly preferable apply in particular for the reaction of a compound of formula (IIa), in which $R^1$ represents methyl (and thus corresponds to the hereinbelow-defined compound of formula (IIb)) and $R^2$ represents $(C_1-C_6)$-alkyl, with the acrolein cyanohydrin esters of formula (IIIa).

In a process preferred in accordance with the invention the metered streams (D1) and (D2) defined in the context of the present invention are metered into the reactor (i.e. the reaction vessel) from separate (i.e. spatially removed) receptacles.

In the process according to the invention preferably at least a portion of the altogether employed entirety of the free-radical-forming substances (IV) is mixed with at least a portion of the altogether employed entirety of the compounds of formula (II)/(IIa) before the resulting metered stream (D1) is metered into the reactor.

A preferred process according to the invention is characterized in that two separate metered streams (D1) and (D2) are metered into the reactor and these metered streams (D1) and (D2) have the following composition:
metered stream (D1) comprises one or more compounds of formula (II) and one or more free-radical-forming substances (IV)
and
metered stream (D2) comprises one or more compounds of formula (III) and also optionally one or more compounds of formula (II) and optionally one or more free-radical-forming substances (IV).

A preferred process according to the invention is characterized in that
metered stream (D1) comprises one or more compounds of formula (II) and one or more free-radical-forming substances (IV), wherein metered stream (D1) comprises 10-100 mol % of the entirety of the amount of the free-radical-forming substances (IV) altogether employed in the reaction.

A preferred process according to the invention is characterized in that metered stream (D1) comprises 20-100 mol % of the entirety of the amount of the free-radical-forming substances (IV) altogether employed in the reaction, by preference 25-100 mol %, preferably 30-100 mol %.

The process according to the invention is preferably characterized in that two separate metered streams (D1) and (D2) are metered into the reactor and these metered streams (D1) and (D2) have the following composition:
metered stream (D1) comprises one or more compounds of formula (II) and one or more free-radical-forming substances (IV), wherein metered stream (D1) comprises 25-100 mol % of the entirety of the amount of the free-radical-forming substances (IV) altogether employed in the reaction
and
metered stream (D2) comprises one or more compounds of formula (III) and also optionally one or more compounds of formula (II) and optionally one or more free-radical-forming substances (IV).

Furthermore, in the process according to the invention preferably at least a portion of the altogether employed entirety of the compounds of formula (II)/(IIa) is mixed with the compound(s) of formula (III)/(IIIa) and optionally in addition with one or more free-radical-forming substances (IV) before the resulting metered stream (D2) is metered into the reactor.

A preferred process according to the invention is characterized in that
metered stream (D1) comprises 30-100 mol % of the entirety of the amount of the free-radical-forming substances (IV) altogether employed in the reaction, by preference 40-100 mol %, preferably 50-100 mol %, more preferably 60-100 mol %, yet more preferably 70-100 mol %, particularly preferably 80-100 mol %, especially preferably 90-100 mol % and most preferably 95-100 mol %.

A more preferred process according to the invention is characterized in that metered stream (D1) comprises 80-100 wt %, preferably 90-100 wt %, preferably 95-100 wt %, especially preferably 100 wt %, of the entirety of the amount of compounds of formula (II) altogether employed in the metered streams (D1) and (D2).

An alternative preferred embodiment of the process according to the invention is characterized in that metered stream (D1) comprises 10-90 wt %, preferably 20-80 wt %, more preferably 25-75 wt %, particularly preferably 30-70 wt % and especially preferably 40-60 wt % of the entirety of the amount of compounds of formula (II) altogether employed in the metered streams (D1) and (D2).

A preferred process according to the invention is characterized in that
metered stream (D2) comprises 80-100 wt %, preferably 90-100 wt %, preferably 95-100 wt %, especially preferably 100 wt %, of the entirety of the amount of compounds of formula (III) altogether employed in the metered streams (D1) and (D2).

A particularly preferred process according to the invention is characterized in that
metered stream (D1) comprises 40-100 mol %, by preference 50-100 mol %, preferably 60-100 mol %, more preferably 70-100 mol %, especially preferably 80-100 mol % and particularly preferably 90-100 mol % of the entirety of the amount of the free-radical-forming substances (IV) altogether employed in the metered streams (D1) and (D2)
and/or
metered stream (D2) comprises 0-60 mol %, by preference 0-50 mol %, preferably 0-40 mol %, more preferably 0-30 mol %, especially preferably 0-20 mol % and particularly preferably 0-10 mol % of the entirety of the amount of the free-radical-forming substances (IV) altogether employed in the metered streams (D1) and (D2).

In a particularly preferred embodiment the process according to the invention is characterized in that
metered stream (D1) comprises 90-100 mol %, by preference 95-100 mol %, preferably 97-100 mol %, more preferably 98-100 mol %, of the entirety of the amount of the free-radical-forming substances (IV) altogether employed in the metered streams (D1) and (D2)
and
metered stream (D2) comprises 0-10 mol %, by preference 0-5 mol %, preferably 0-3 mol %, more preferably 0-2 mol %, of the entirety of the amount of the free-radical-forming substances (IV) altogether employed in the metered streams (D1) and (D2).

In a particularly preferred embodiment the process according to the invention is characterized in that
metered stream (D1) comprises 99-100 mol %, preferably 100 mol %, of the entirety of the amount of the free-radical-forming substances (IV) altogether employed in the metered streams (D1) and (D2)
and
metered stream (D2) comprises 0-1 mol %, preferably 0 mol %, of the entirety of the amount of the free-radical-forming substances (IV) altogether employed in the metered streams (D1) and (D2).

A particularly preferred process according to the invention is characterized in that the entirety of the compounds (II) and (IV) in the metered stream (D1) is 75 to 100 wt %, preferably 80 to 100 wt %, more preferably 85 to 100 wt %, particularly preferably 90 to 100 wt %, in each case based on the total weight of the metered stream (D1).

The process according to the invention is preferably carried out under conditions in which free-radicals are formed.

The reaction of the compounds of formula (II) and (III)/of formula (IIa) and (IIIa) to afford the compounds of formula (I)/(Ia) in a process according to the invention is preferably effected with the aid of a free-radical-forming source, for example using electromagnetic fields such as UV radiation, gamma radiation or X-rays, electric fields or electrochemical methods or in the presence of one or more free-radical-forming substances.

In the context of the process according to the invention it is preferable to employ free-radical-forming substances.

A preferred process according to the invention is characterized in that one, more than one or all of the free-radical-forming substances (IV) conform to formula (V)

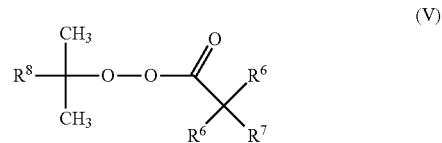

wherein
R$^6$ independently at each occurrence represents hydrogen, (C$_1$-C$_{10}$)-alkyl, by preference (C$_1$-C$_6$)-alkyl, preferably (C$_1$-C$_4$)-alkyl,
R$^7$ represents hydrogen or (C$_1$-C$_{10}$)-alkyl, by preference hydrogen or (C$_1$-C$_6$)-alkyl, preferably hydrogen or (C$_1$-C$_4$)-alkyl,
and
R$^8$ represents methyl, ethyl, 2,2-dimethylpropyl or phenyl.

Preferred free-radical-forming substances of formula (V) are those in which
R$^6$ independently at each occurrence represents (C$_1$-C$_{10}$)-alkyl, by preference (C$_1$-C$_6$)-alkyl, preferably (C$_1$-C$_4$)-alkyl,
R$^7$ represents hydrogen or (C$_1$-C$_{10}$)-alkyl, by preference hydrogen or (C$_1$-C$_6$)-alkyl, preferably hydrogen or (C$_1$-C$_4$)-alkyl,
and
R$^8$ represents methyl, ethyl, 2,2-dimethylpropyl or phenyl.

The free-radical-formers (radical initiators) of formula (V) are known per se and in some cases commercially available.

The free-radical-formers of formula (V) in this context are preferably selected from the group consisting of tert-butyl peroxypivalate, tert-amyl peroxypivalate, tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2-ethylhexanoate, tert-amyl peroxyneodecanoate, cumyl peroxyneodecanoate, cumyl peroxyneoheptanoate, cumyl peroxypivalate and mixtures thereof.

The free-radical-formers of formula (V) in this context are preferably selected from the group consisting of tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2-ethylhexanoate, cumyl peroxyneodecanoate and mixtures thereof, particular preference in turn being given to 1,1,3,3-tetramethylbutyl peroxyneodecanoate, tert-butyl peroxyneodecanoate and/or tert-butyl peroxy-2-ethylhexanoate.

The process according to the invention allows production of the phosphorus-containing cyanohydrin esters of formula (I) or (Ia)/of hereinbelow-defined formula (Ib) under mild reaction conditions and in a manner that is simpler to carry out in terms of process/plant engineering. The phosphorus-containing cyanohydrin esters of formula (I), (Ia) and (Ib) can therefore be obtained more easily in process engineering terms, in even better yields and in high purity.

The process according to the invention is preferably carried out such that the metered streams (D1) and (D2) are metered into the reactor predominantly simultaneously, preferably simultaneously.

The process according to the invention is preferably carried out such that the reaction is effected at a temperature in the range from 40° C. to 120° C., preferably at a temperature in the range from 50° C. to 110° C., more preferably at a temperature in the range from 55° C. to 100° C. and particularly preferably at a temperature in the range from 60° C. to 95° C.

Performing the process according to the invention thus significantly reduces or largely avoids a disproportionation of reactants of formula (II)/(IIa) for example. Performing the process according to the invention also significantly reduces or largely avoids the oligomerization and polymerization of the compounds of formula (III)/(IIIa).

It is advantageous in the context of the process according to the invention to employ the cyanohydrin esters of formula (III)/(IIIa) in the highest possible purity. It is preferable when the cyanohydrin esters of formula (III)/(IIIa) are employed in a purity of not less than 90 wt %, preferably of not less than 92 wt %, more preferably of not less than 95 wt %, especially preferably of not less than 98 wt %.

The formed phosphorus-containing cyanohydrin esters of formula (I)/(Ia)/hereinbelow-defined formula (Ib) may be used as starting materials for the synthesis of phosphorus-containing amino acids, for example glufosinate (such a synthesis route is more particularly described hereinbelow).

To avoid undesired side reactions and thus to achieve high yields it is additionally advantageous to employ the phosphorus-containing reactant (II)/(IIa) in a molar excess based on the cyanohydrin esters of formula (III)/(IIIa).

The process according to the invention in these preferred embodiments further has the advantage that no large excesses of compounds of formula (II)/(IIa) based on the employed entirety of compounds of formula (III)/(IIIa) are required to achieve the advantageous effects of the process according to the invention.

Preferably, in the process according to the invention the molar ratio of the entirety of the employed compound of formula (II)/(IIa) to the entirety of the employed compound of formula (III)/(IIIa) is in the range from 8:1 to 1:1, preferably in the range from 5:1 to 2:1.

Preferably, in the process according to the invention the molar ratio of the entirety of the employed compound of formula (II)/(IIa) to the entirety of the employed compound of formula (III)/(IIIa) is in the range from 5:1 to 5:2, more preferably in the range from 9:2 to 5:2.

Particularly preferred embodiments of the process according to the invention for producing the compounds of formula (I) by reaction of a compound of formula (II) with the acrolein cyanohydrin ester of formula (III) are characterized in that metered stream (D1) comprises 30-100 mol % of the entirety of the amount of the free-radical-forming substances (IV) altogether employed in the reaction, by preference 40-100 mol %, preferably 50-100 mol %, more preferably 60-100 mol %, yet more preferably 70-100 mol %, particularly preferably 80-100 mol %, especially preferably 90-100 mol % and most preferably 95-100 mol %, the entirety of the compounds (II) and (IV) in the metered stream (D1) is 75 to 100 wt %, preferably 80 to 100 wt %, more preferably 85 to 100 wt %, particularly preferably 90 to 100 wt %, in each case based on the total weight of the metered stream (D1), the molar ratio of the entirety of the employed compound of formula (II) to the entirety of the employed compound of formula (III) is in the range from 8:1 to 1:1, preferably in the range from 5:1 to 2:1 and the reaction is effected at a temperature in the range from 40° C. to 120° C., preferably at a temperature in the range from 50° C. to 110° C., more preferably at a temperature in the range from 55° C. to 100° C. and particularly preferably at a temperature in the range from 60° C. to 95° C.

Particularly preferred embodiments of the process according to the invention for producing the compounds of formula (I) by reaction of a compound of formula (II) with the acrolein cyanohydrin ester of formula (III) are characterized in that metered stream (D1) comprises 40-100 mol %, by preference 50-100 mol %, preferably 60-100 mol %, more preferably 70-100 mol %, especially preferably 80-100 mol % and particularly preferably 90-100 mol % of the entirety of the amount of the free-radical-forming substances (IV) altogether employed in the metered streams (D1) and (D2), metered stream (D2) comprises 0-60 mol %, by preference 0-50 mol %, preferably 0-40 mol %, more preferably 0-30 mol %, especially preferably 0-20 mol % and particularly preferably 0-10 mol % of the entirety of the amount of the free-radical-forming substances (IV) altogether employed in the metered streams (D1) and (D2), the entirety of the compounds (II) and (IV) in the metered stream (D1) is 75 to 100 wt %, preferably 80 to 100 wt %, more preferably 85 to 100 wt %, particularly preferably 90 to 100 wt %, in each case based on the total weight of the metered stream (D1), the molar ratio of the entirety of the employed compound of formula (II) to the entirety of the employed compound of formula (III) is in the range from 8:1 to 1:1, preferably in the range from 5:1 to 2:1, wherein one, more than one or all of the free-radical-forming substances (IV) conform to formula (V) and are preferably selected from the group consisting of tert-butyl peroxypivalate, tert-amyl peroxypivalate, tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2-ethylhexanoate, tert-amyl peroxyneodecanoate, cumyl peroxyneodecanoate, cumyl peroxyneoheptanoate, cumyl peroxypivalate and mixtures thereof and the reaction is effected at a temperature in the range from 40° C. to 120° C., preferably at a temperature in the range from 50° C. to 110° C., more preferably at a temperature in the range from 55° C. to 100° C. and particularly preferably at a temperature in the range from 60° C. to 95° C.

Particularly preferred embodiments of the process according to the invention for producing the compounds of formula (I) by reaction of a compound of formula (II) with the acrolein cyanohydrin ester of formula (III), in particular for producing the compounds of formula (Ia) by reaction of a compound of formula (IIa) with the acrolein cyanohydrin ester of formula (IIIa) are characterized in that metered stream (D1) comprises 50-100 mol %, preferably 60-100 mol %, more preferably 70-100 mol %, especially preferably 80-100 mol % and particularly preferably 90-100 mol % of the entirety of the amount of the free-radical-forming substances (IV) altogether employed in the metered streams (D1) and (D2), metered stream (D2) comprises 0-50 mol %, preferably 0-40 mol %, more preferably 0-30 mol %, especially preferably 0-20 mol % and particularly preferably 0-10 mol % of the entirety of the amount of the free-radical-forming substances (IV) altogether employed in the metered streams (D1) and (D2), the entirety of the compounds (II)/(IIa) and (IV) in the metered stream (D1) is 80 to 100 wt %, preferably 85 to 100 wt %, particularly preferably 90 to 100 wt %, in each case based on the total weight of the metered stream (D1), the molar ratio of the entirety of the employed compound of formula (II)/(IIa) to the entirety of the employed compound of formula (III)/(IIIa) is in the range from 5:1 to 2:1, wherein one, more than one or all of the free-radical-forming substances (IV) conform to formula (V) and are preferably selected from the group consisting of tert-butyl peroxypivalate, tert-amyl peroxypivalate, tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2-ethylhexanoate, tert-amyl peroxyneodecanoate, cumyl peroxyneodecanoate, cumyl peroxyneoheptanoate, cumyl peroxypivalate and mixtures thereof and the reaction is effected at a temperature in the range from 50° C. to 110° C., preferably at a temperature in the range from 55° C. to 100° C. and particularly preferably at a temperature in the range from 60° C. to 95° C.

Particularly preferred embodiments of the process according to the invention for producing the compounds of formula (I) by reaction of a compound of formula (II) with the acrolein cyanohydrin ester of formula (III), in particular for producing the compounds of formula (Ia) by reaction of a compound of formula (IIa) with the acrolein cyanohydrin ester of formula (IIIa) are characterized in that metered stream (D1) comprises 70-100 mol %, especially preferably 80-100 mol % and particularly preferably 90-100 mol % of the entirety of the amount of the free-radical-forming substances (IV) altogether employed in the metered streamss (D1) and (D2), metered stream (D2) comprises 0-30 mol %, especially preferably 0-20 mol % and particularly preferably 0-10 mol % of the entirety of the amount of the free-radical-forming substances (IV) altogether employed in the metered streams (D1) and (D2), the entirety of the compounds (II)/(IIa) and (IV) in the metered stream (D1) is 80 to 100 wt %, preferably 85 to 100 wt %, particularly preferably 90 to 100 wt %, in each case based on the total weight of the metered stream (D1), the molar ratio of the entirety of the employed compound of formula (II)/(IIa) to the entirety of the employed compound of formula (III)/(IIIa) is in the range from 5:1 to 2:1, wherein one, more than one or all of the free-radical-forming substances (IV) conform to formula (V) and are selected from the group consisting of tert-butyl peroxypivalate, tert-amyl peroxypivalate, tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2-ethylhexanoate, tert-amyl peroxyneodecanoate, cumyl peroxyneodecanoate, cumyl peroxyneoheptanoate, cumyl peroxypivalate and mixtures thereof and the reaction is effected at a temperature in the range from 50° C. to 110° C., preferably at a temperature in the range from 55° C. to 100° C. and particularly preferably at a temperature in the range from 60° C. to 95° C.

Especially preferred embodiments of the process according to the invention for producing the compounds of formula (Ia) by reaction of a compound of formula (IIa) with the acrolein cyanohydrin ester of formula (IIIa) are characterized in that metered stream (D1) comprises 70-100 mol %, especially preferably 80-100 mol % and particularly preferably 90-100 mol % of the entirety of the amount of the free-radical-forming substances (IV) altogether employed in the metered streams (D1) and (D2), metered stream (D2) comprises 0-30 mol %, especially preferably 0-20 mol % and particularly preferably 0-10 mol % of the entirety of the amount of the free-radical-forming substances (IV) altogether employed in the metered streams (D1) and (D2), the entirety of the compounds (IIa) and (IV) in the metered stream (D1) is 80 to 100 wt %, preferably 85 to 100 wt %, particularly preferably 90 to 100 wt %, in each case based on the total weight of the metered stream (D1), the molar ratio of the entirety of the employed compound of formula (IIa) to the entirety of the employed compound of formula (IIIa) is in the range from 5:1 to 2:1, wherein one, more than one or all of the free-radical-forming substances (IV) conform to formula (V) and are selected from the group consisting of tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2-ethylhexanoate, cumyl peroxyneodecanoate and mixtures thereof, particular preference in turn being given to 1,1,3,3-tetramethylbutyl peroxyneodecanoate, tert-butyl peroxyneodecanoate and/or tert-butyl peroxy-2-ethylhexanoate and the reaction is effected at a temperature in the range from 50° C. to 110° C., preferably at a temperature in the range from 55° C. to 100° C. and particularly preferably at a temperature in the range from 60° C. to 95° C.

Especially preferred embodiments of the process according to the invention for producing the compounds of formula (Ia) by reaction of a compound of formula (IIa) with the acrolein cyanohydrin ester of formula (IIIa) are characterized in that metered stream (D1) comprises 80-100 mol %, preferably 90-100 mol %, of the entirety of the amount of the free-radical-forming substances (IV) altogether employed in the metered streams (D1) and (D2), metered stream (D2) comprises 0-20 mol %, preferably 0-10 mol %, of the entirety of the amount of the free-radical-forming substances (IV) altogether employed in the metered streams (D1) and (D2), the entirety of the compounds (IIa) and (IV) in the metered stream (D1) is 85 to 100 wt %, preferably 90 to 100 wt %, in each case based on the total weight of the metered stream (D1), the molar ratio of the entirety of the employed compound of formula (IIa) to the entirety of the employed compound of formula (IIIa) is in the range from 5:1 to 5:2, wherein one, more than one or all of the free-radical-forming substances (IV) conform to formula (V) and are selected from the group consisting of tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2ethylhexanoate, cumyl peroxyneodecanoate and mixtures thereof, particular preference in turn being given to 1,1,3,3-tetramethylbutyl peroxyneodecanoate, tert-butyl peroxyneodecanoate and/or tert-butyl peroxy-2-ethylhexanoate
and
the reaction is effected at a temperature in the range from 50° C. to 110° C., preferably at a temperature in the range from 55° C. to 100° C. and particularly preferably at a temperature in the range from 60° C. to 95° C.

Especially preferred embodiments of the process according to the invention for producing the compounds of formula (Ia) by reaction of a compound of formula (IIa), in which $R^1$ represents methyl (and thus corresponds to the hereinbelow-defined compound of formula (IIb)) and $R^2$ represents ($C_1$-$C_6$)-alkyl, with the acrolein cyanohydrin esters of formula (IIIa) are characterized in that
metered stream (D1) comprises 90-100 mol %, by preference 95-100 mol %, preferably 97-100 mol %, more preferably 98-100 mol %, of the entirety of the amount of the free-radical-forming substances (IV) altogether employed in the metered streams (D1) and (D2),
metered stream (D2) comprises 0-10 mol %, by preference 0-5 mol %, preferably 0-3 mol %, more preferably 0-2 mol %, of the entirety of the amount of the free-radical-forming substances (IV) altogether employed in the metered streams (D1) and (D2),
the entirety of the compounds (IIa) and (IV) in the metered stream (D1) is 85 to 100 wt %, preferably 90 to 100 wt %, in each case based on the total weight of the metered stream (D1),
the molar ratio of the entirety of the employed compound of formula (IIa) to the entirety of the employed compound of formula (IIIa) is in the range from 5:1 to 5:2,
wherein one, more than one or all of the free-radical-forming substances (IV) conform to formula (V) and are selected from the group consisting of tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2-ethylhexanoate, cumyl peroxyneodecanoate and mixtures thereof, particular preference in turn being given to 1,1,3,3-tetramethylbutyl peroxyneodecanoate, tert-butyl peroxyneodecanoate and/or tert-butyl peroxy-2-ethylhexanoate
and
the reaction is effected at a temperature in the range from 55° C. to 100° C., particularly preferably at a temperature in the range from 60° C. to 95° C.

Especially preferred embodiments of the process according to the invention for producing the compounds of formula (Ia) by reaction of a compound of formula (IIa), in which $R^1$ represents methyl (and thus corresponds to the hereinbelow-defined compound of formula (IIb)) and $R^2$ represents ($C_1$-$C_6$)-alkyl, with the acrolein cyanohydrin esters of formula (IIIa) are characterized in that
metered stream (D1) comprises 90-100 mol %, by preference 95-100 mol %, preferably 97-100 mol %, more preferably 98-100 mol %, of the entirety of the amount of the free-radical-forming substances (IV) altogether employed in the metered streams (D1) and (D2),
metered stream (D2) comprises 0-10 mol %, by preference 0-5 mol %, preferably 0-3 mol %, more preferably 0-2 mol %, of the entirety of the amount of the free-radical-forming substances (IV) altogether employed in the metered streams (D1) and (D2),
the entirety of the compounds (IIa) and (IV) in the metered stream (D1) is 85 to 100 wt %, preferably 90 to 100 wt %, in each case based on the total weight of the metered stream (D1),
the molar ratio of the entirety of the employed compound of formula (IIa) to the entirety of the employed compound of formula (IIIa) is in the range from 9:2 to 5:2,
wherein one, more than one or all of the free-radical-forming substances (IV) conform to formula (V) and are selected from the group consisting of tert-butyl peroxyneodecanoate, 1,1,3,3-tetramethylbutyl peroxyneodecanoate, tert-butyl peroxy-2-ethylhexanoate, 1,1,3,3-tetramethylbutyl peroxy-2-ethylhexanoate, cumyl peroxyneodecanoate and mixtures thereof, particular preference in turn being given to 1,1,3,3-tetramethylbutyl peroxyneodecanoate, tert-butyl peroxyneodecanoate and/or tert-butyl peroxy-2-ethylhexanoate
and
the reaction is effected at a temperature in the range from 55° C. to 100° C., particularly preferably at a temperature in the range from 60° C. to 95° C.

Especially preferred embodiments of the process according to the invention for producing the compounds of formula (Ia) by reaction of a compound of formula (IIa), in which $R^1$ represents methyl (and thus corresponds to the hereinbelow-defined compound of formula (IIb)) and $R^2$ represents ($C_1$-$C_6$)-alkyl, with the acrolein cyanohydrin ester of formula (IIIa) are characterized in that
metered stream (D1) comprises 95-100 mol %, preferably 97-100 mol %, more preferably 98-100 mol % of the entirety of the amount of the free-radical-forming substances (IV) altogether employed in the metered streams (D1) and (D2),
metered stream (D2) comprises 0-5 mol %, preferably 0-3 mol %, more preferably 0-2 mol % of the entirety of the amount of the free-radical-forming substances (IV) altogether employed in the metered streams (D1) and (D2),
the entirety of the compounds (IIa) and (IV) in the metered stream (D1) is 90 to 100 wt % based on the total weight of the metered stream (D1),
the molar ratio of the entirety of the employed compound of formula (IIa) to the entirety of the employed compound of formula (IIIa) is in the range from 9:2 to 5:2,
wherein all of the free-radical-forming substances (IV) conform to formula (V) and are selected from the group consisting of 1,1,3,3-tetramethylbutyl peroxyneodecanoate, tert-butyl peroxyneodecanoate, tert-butyl peroxy-2-ethylhexanoate and mixtures thereof
and
the reaction is effected at a temperature in the range from 55° C. to 100° C., particularly preferably at a temperature in the range from 60° C. to 95° C.

Especially preferred embodiments of the process according to the invention for producing the compounds of formula (Ia) by reaction of a compound of formula (IIa), in which $R^1$ represents methyl (and thus corresponds to the hereinbelow-defined compound of formula (IIb)) and $R^2$ represents ($C_1$-$C_6$)-alkyl, with the acrolein cyanohydrin ester of formula (IIIa) are characterized in that
metered stream (D1) comprises 97-100 mol %, preferably 98-100 mol %, of the entirety of the amount of the free-radical-forming substances (IV) altogether employed in the metered streams (D1) and (D2),
metered stream (D2) comprises 0-3 mol %, preferably 0-2 mol %, of the entirety of the amount of the free-radical-forming substances (IV) altogether employed in the metered streams (D1) and (D2), the entirety of the compounds (IIa) and (IV) in the metered stream (D1) is 90 to 100 wt % based on the total weight of the metered stream (D1),
the molar ratio of the entirety of the employed compound of formula (IIa) to the entirety of the employed compound of formula (IIIa) is in the range from 9:2 to 5:2,
wherein all of the free-radical-forming substances (IV) conform to formula (V) and are selected from the group consisting of 1,1,3,3-tetramethylbutyl peroxyneodecanoate, tert-butyl peroxyneodecanoate, tert-butyl peroxy-2-ethylhexanoate and mixtures thereof
and
the reaction is effected at a temperature in the range from 60° C. to 95° C.

The process according to the invention may be carried out either in a discontinuous process regime (for example in a semibatch mode of operation) or else in a continuous process regime (for example in a continuously operated stirred tank).

In the context of the present invention a continuous process regime is to be understood as meaning that compounds (i.e. reactants such as compounds of formula (II) and (III)) are brought into the reactor (feeding/influx) while at the same time, but spatially removed therefrom, compounds (i.e. products such as compounds of formula (I)) are brought out of the reactor (discharging/efflux).

In a discontinuous process regime by contrast, the steps of feeding of reactants (i.e. of reactants such as compounds of formula (II) and (III)), reaction (i.e. reaction of the reactants) and discharging of the products (i.e. products such as compounds of formula (I)) from the reactor are effected consecutively or overlapping only in individual stages.

The process according to the invention is preferably carried out such that the metering of the metered streams (D1) and (D2) into the reactor is effected substantially continuously, preferably continuously.

Such a substantially continuous or preferably continuous process regime is economically advantageous since, for example, unproductive reactor times due to filling and emptying processes and lengthened reaction times due to safety engineering reasons, reactor-specific heat exchange performances and heating and cooling processes such as are encountered in semi-batch processes and batch processes can be avoided/minimized.

The process according to the invention is preferably carried out under inertization, preferably in a protective gas atmosphere. Preferred protective gases are nitrogen/argon.

It is further possible to carry out the process according to the invention under superatmospheric pressure or under reduced pressure.

The process according to the invention may be carried out in an optional diluent.

Usable optional diluents in principle include various organic solvents, preferably toluene, xylene, chlorobenzene, dichlorobenzene, dimethyl formamide (DMF), dimethylacetamide, N-methyl-2-pyrrolidone (NMP) or mixtures of these organic solvents. The process according to the invention is preferably carried out without such further optional solvents.

However, it may be advantageous to carry out the process according to the invention in previously formed reaction product of formula (I), (Ia) or (Ib) as diluent.

In a continuous mode of operation in particular it is advantageous to carry out the process according to the invention in previously formed reaction product of formula (I), (Ia) or (Ib) or in a mixture of reaction product of formula (I), (Ia) or (Ib) and reactant of formula (II)/(IIa) as diluent.

The purity of the desired products of formula (I) after purification, for example after distillative removal of an excess of the component (II)/(IIa), is regularly greater than 95%. A preferably recovered excess of the starting compound (II)/(IIa) may subsequently be reemployed in the same reaction without further purification.

This applies in particular for the compound of formula (Ib) where $R^2$=n-butyl which is obtained by the process according to the invention by reaction of the phosphorus-containing reactant (IIa) where $R^1$=methyl and $R^2$=n-butyl with acrolein cyanohydrin-O-acetate of formula (IIIa).

Glufosinate salts in the context of the present invention are preferably ammonium salts, phosphonium salts, sulphonium salts, alkali metal salts and alkaline earth metal salts of glufosinate.

Especially preferred in the context of the present invention are glufosinate, glufosinate sodium and glufosinate ammonium.

In a further aspect the present invention relates to the production of glufosinate

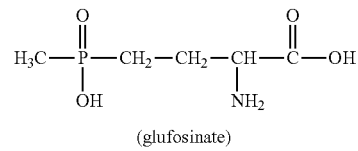

(glufosinate)

or glufosinate salts (preferably glufosinate ammonium) characterized in that in this process a compound of formula (Ib) is employed

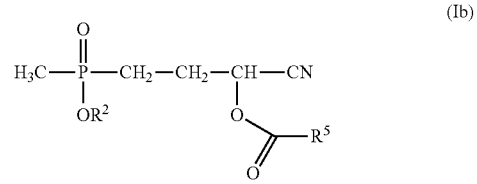

(Ib)

wherein $R^2$ has the meaning defined in accordance with the invention hereinabove, preferably the meaning defined as preferable hereinabove and particularly preferably the meaning defined as particularly preferable hereinabove
and
$R^5$ has the meaning recited hereinabove and preferably represents methyl and
the production of the compound of formula (Ib) is effected by a process defined in accordance with the invention.

In a preferred aspect the present invention relates to the production of glufosinate and/or glufosinate salts

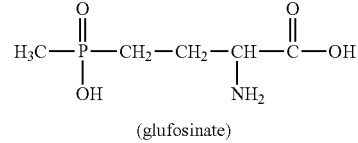

(glufosinate)

characterized by reaction of a compound of formula (Ib) by the following step:
reaction of a compound of formula (IIb)

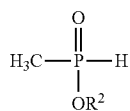

(IIb)

wherein —R² represents (C₁-C₆)-alkyl, preferably (C₄-C₅)-alkyl and particularly preferably n-butyl or n-pentyl, with acrolein cyanohydrin-O-acetate of formula (IIIA)

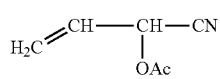

(IIIa)

wherein the reaction of (IIb) with (IIIa) is effected by the hereinabove-described process according to the invention, preferably in one of the embodiments described as preferable and particularly preferably in one of the embodiments described as particularly preferable.

The process according to the invention for producing glufosinate and/or glufosinate salts is further preferably effected by reaction of a compound of formula (Ib) with NH₃ to afford compound (VI),

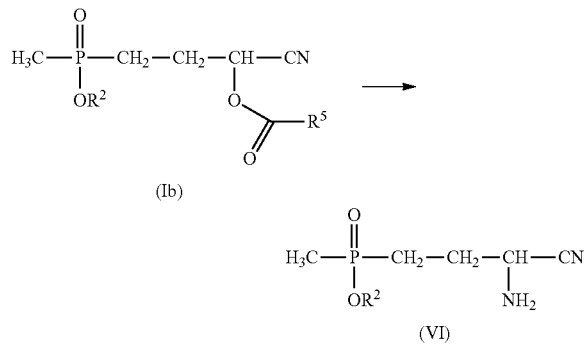

wherein R² and R⁵ each have the meaning recited hereinabove, and subsequent hydrolysis of compound (VI) to afford glufosinate/the salts thereof.

The process according to the invention for producing glufosinate and/or glufosinate salts may be effected in similar fashion as described for example in U.S. Pat. No. 4,521,348.

Finally, the present invention also relates to the use of a compound of formula (I)/(Ib) as defined hereinabove and produced by a process according to the invention for producing glufosinate/glufosinate salts, in particular glufosinate, glufosinate sodium or glufosinate ammonium.

The present invention further relates to a process for producing glufosinate/glufosinate salts, in particular glufosinate, glufosinate sodium or glufosinate ammonium, comprising the following steps (a) and (b):
(a) producing of a compound of formula (I)/(Ib) as defined hereinabove,
(b) use of the compound of formula (I)/(Ib) obtained in step (a) for producing glufosinate/glufosinate salts, in particular glufosinate, glufosinate sodium or glufosinate ammonium.

The examples which follow elucidate the present invention.

EXAMPLES

All data are based on weight unless otherwise stated.

Abbreviations Used

MPE: methanephosphonous acid mono-n-butyl ester
ACA: acrolein cyanohydrin acetate
ACM: n-butyl (3-cyano-3-acetoxypropyl)methylphosphinate Example 1 n-butyl (3-cyano-3-acetoxypropyl)methylphosphinate (ACM) (Noninventive)

Discontinuous Mode of Operation

A temperature-controllable, cylindrical glass reactor was filled with a portion of the required MPE to adequately cover the stirring means and the reactor contents were brought to reaction temperature (typically 85° C.). In the experiments with a pumped circulation system/circulation loop, the circulation loop including the associated pump was also filled with MPE. Commixing of the reactor contents was accomplished via a six-blade disc stirrer in combination with four baffles. The reactor contents were always blanketed with nitrogen and the reactor was operated without application of superatmospheric pressure.

To ensure reliable starting of the reaction (i.e. reliable initiation), 5 minutes before commencement of the metering of the reactants into the reactor a small amount of initiator (0.9-1.0 mL, corresponding to about 0.8-0.9 g) was injected into the initially charged MPE previously heated to reaction temperature (and possibly also circulating through the circulation loop). The time interval of 5 minutes corresponds approximately to the half-life of the free-radical initiator tert-butyl perneodecanoate at 85° C. Toward the end of the metering time of 4 hours (i.e. more than 40 half-lives of the employed free-radical initiator) the initially injected amount of tert-butyl perneodecanoate had fallen to <10⁻¹² parts of the starting amount and thus had no appreciable further relevance for the ACM production in the continuous mode of operation according to hereinbelow-reported example 2.

The reactants E1 and E2 were then separately metered into the reactor until the desired fill-level had been achieved, taking into account the respective stoichiometries.

142.0 g of MPE (98% purity) were initially charged and heated to 85° C. 5 min before commencement of the metering of the reactants E1 and E2, 1.0 ml (about 0.9 g) of the free-radical initiator tert-butyl perneodecanoate (98% purity) was added. The following reactants E1 and E2 were then simultaneously metered into the reactor over a period of 4.0 h:
reactants E1 was a mixture of MPE (102.1 g, 98% purity) and tert-butyl perneodecanoate (3.0 g, 98% purity), reactant E2 was composed of 57.0 g of ACA (99% purity).

The concentration of the free-radical initiator was accordingly 1.0 wt % based on the overall mixture.

After expiry of the metering time the discontinuous batch had reached its endpoint; the employed ACA had reacted completely.

Example 2 n-butyl (3-cyano-3-acetoxypropyl)methylphosphinate (ACM) (Noninventive)

Continuous Mode of Operation

The reactor was initially charged with a mixture produced by the discontinuous mode of operation according to hereinabove-reported example 1. The reaction conditions and the apparatus parameters were the same as those from example 1. At a reaction temperature of 85° C., the metered streams (D1) and (D2) were then simultaneously and separately metered into the reactor.

At 85° C., metered stream (D1), a mixture of MPE and free-radical initiator tert-butyl perneodecanoate, was added to the reactor at 63 mL/h and metered stream (D2), ACA, was added to the reactor at 14 mL/h, the content of the free-radical initiator in the MPE (1.2 wt %) being chosen such that a content of 1.0 wt % of free-radical initiator in the overall mixture in the reactor was achieved.

Corresponding to the supplied volume flows, an adequately large volume flow of the reactor mixture was withdrawn from the reactor to keep the fill-volume in the reactor constant. The fill-volume in the reactor and the supplied/discharged volume flows resulted in an average hydrodynamic residence time of 4.0 hours in the reactor.

Once a steady-state had been achieved, samples of the reactor contents were withdrawn and a yield of 95-96% for the reaction of ACA to afford ACM was determined.

Example 3 n-butyl (3-cyano-3-acetoxypropyl)methylphosphinate (ACM)

Continuous Mode of Operation

The reactor was initially charged with a mixture produced by the discontinuous mode of operation according to hereinabove-reported example 1. The reaction conditions and the apparatus parameters were the same as those from example 1. At a reaction temperature of 85° C., the metered streams (D1) and (D2) were then simultaneously and separately metered into the reactor.

At 85° C., metered stream (D1), a mixture of MPE and free-radical initiator tert-butyl perneodecanoate, was added to the reactor at 63 mL/h and metered stream (D2), ACA, was added to the reactor at 14 mL/h, the content of the free-radical initiator in the MPE (1.2 wt %) being chosen such that a content of 1.0 wt % of free-radical initiator in the overall mixture in the reactor was achieved.

Corresponding to the supplied volume flows, an adequately large volume flow of the reactor mixture was withdrawn from the reactor to keep the fill-volume in the reactor constant. The fill-volume in the reactor and the supplied/discharged volume flows resulted in an average hydrodynamic residence time of 4.0 hours in the reactor.

The metered streams were supplied to the reaction mixture in the pumped circulation system/circulation loop of the stirred vessel via static mixers. Commixing of the reactor contents was furthermore accomplished via a six-blade disc stirrer in combination with four baffles.

Using various static mixers having structures on the millimetre and/or micrometre scale (for example Sulzer SMX, EMB cascade mixer) for a wide variety of volume flows in the pumped circulation system, mixing times (for a CoV of <0.01) of up to <1 s, in some cases even up to <0.1 s, were achieved in the static mixers. The specific power inputs (based on the total volume of the condensed phase in the reactor) for the static mixers varied from >0.001 W/L to <10 W/L (1 W/L=1 kW/m$^3$).

Once a steady-state had been achieved, for mixing times of <1 s (in the static mixers) and specific power inputs of >0.1 W/L (based on the total volume of the condensed phase in the reactor), samples of the reactor contents were withdrawn and a yield of 98% for the reaction of ACA to afford ACM was determined.

The invention claimed is:
1. Process for producing a compound of formula (I)

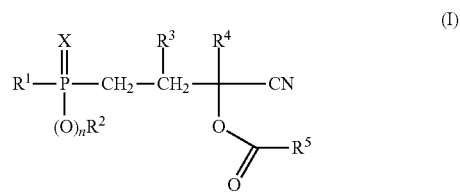

wherein a compound of formula (II)

is reacted with a compound of formula (III)

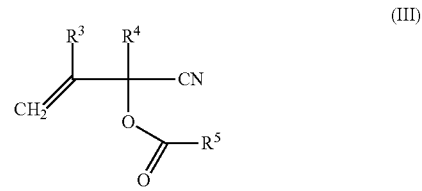

wherein in each case:
$R^1$ represents $(C_1-C_{12})$-alkyl, $(C_1-C_{12})$-haloalkyl, $(C_6-C_{10})$-aryl, $(C_6-C_{10})$-haloaryl, $(C_7-C_{10})$-aralkyl, $(C_7-C_{10})$-haloaralkyl, $(C_4-C_{10})$-cycloalkyl or $(C_4-C_{10})$-halocycloalkyl,
$R^2$ represents $(C_1-C_{12})$-alkyl, $(C_1-C_{12})$-haloalkyl, $(C_6-C_{10})$-aryl, $(C_6-C_{10})$-haloaryl, $(C_7-C_{10})$-aralkyl, $(C_7-C_{10})$-haloaralkyl, $(C_4-C_{10})$-cycloalkyl or $(C_4-C_{10})$-halocycloalkyl,
$R^3$ and $R^4$ each independently of one another represent hydrogen, $(C_1-C_4)$-alkyl, phenyl or benzyl,
$R^5$ represents $(C_1-C_{12})$-alkyl, $(C_1-C_{12})$-haloalkyl, $(C_6-C_{10})$-aryl, $(C_6-C_{10})$-haloaryl, $(C_7-C_{10})$-aralkyl, $(C_7-C_{10})$-haloaralkyl, $(C_4-C_{10})$-cycloalkyl or $(C_4-C_{10})$-halocycloalkyl,
X represents oxygen or sulphur and
n is 0 or 1,
in the presence of one or more free-radical-forming substances (IV) in a reactor with mixing, wherein the mixing is effected under the following parameters:
the specific power input is at least 0.03 kW/m$^3$
and/or the mixing time to achieve a coefficient of variation of 0.01 or lower (CoV≤10⁻²) is less than 10 seconds.

2. Process according to claim 1, wherein the mixing is effected under the following parameters:
the specific power input is at least 0.3 kW/m³
and/or
the mixing time to achieve a coefficient of variation of 0.01 or lower (CoV≤10⁻²) is less than 1 second.

3. Process according to claim 1, wherein the mixing is effected under the following parameters:
the specific power input is at least 3 kW/m³
and/or
the mixing time to achieve a coefficient of variation of 0.01 or lower (CoV≤10⁻²) is less than 0.1 seconds.

4. Process according to claim 1, wherein two separate metered streams (D1) and (D2) are metered into the reactor and these metered streams (D1) and (D2) have the following composition:
metered stream (D1) comprises one or more compounds of formula (II) and one or more free-radical-forming substances (IV)
and
metered stream (D2) comprises one or more compounds of formula (III) and also optionally one or more compounds of formula (II) and optionally one or more free-radical-forming substances (IV).

5. Process according to claim 4, wherein metered stream (D1) comprises one or more compounds of formula (II) and one or more free-radical-forming substances (IV), wherein metered stream (D1) comprises 10-100 mol % of the entirety of the amount of free-radical-forming substances (IV) altogether employed.

6. Process according to claim 4, wherein metered stream (D1) comprises 20-100 mol % of the entirety of the amount of free-radical-forming substances (IV) altogether employed, optionally 25-100 mol %, optionally 30-100 mol %.

7. Process according to claim 4, wherein metered stream (D1) comprises 80-100 wt %, optionally 90-100 wt %, optionally 95-100 wt %, optionally 100 wt %, of the entirety of the amount of compounds of formula (II) altogether employed in the metered streams (D1) and (D2).

8. Process according to claim 4, wherein the metered streams (D1) and (D2) are metered into the reactor predominantly simultaneously, optionally simultaneously.

9. Process according to claim 4, wherein the metering of the metered streams (D1) and (D2) into the reactor is effected substantially continuously, optionally continuously.

10. Process according to claim 1, wherein one, more than one or all of the free-radical-forming substances (IV) conform to formula (V)

$$R^8 - \overset{CH_3}{\underset{CH_3}{C}} - O - O - \overset{O}{\underset{R^7}{\overset{\parallel}{C}}} - \overset{R^6}{\underset{R^7}{C}} - R^6 \quad (V)$$

wherein
$R^6$ independently at each occurrence represents hydrogen, $(C_1-C_{10})$-alkyl, by preference $(C_1-C_6)$-alkyl, optionally $(C_1-C_4)$-alkyl,
$R^7$ represents hydrogen or $(C_1-C_{10})$-alkyl, by preference hydrogen or $(C_1-C_6)$-alkyl, optionally hydrogen or $(C_1-C_4)$-alkyl,
and
$R^8$ represents methyl, ethyl, 2,2-dimethylpropyl or phenyl.

11. Process according to claim 1, wherein the reaction is effected at a temperature in the range from 40° C. to 120° C., optionally at a temperature in the range from 50° C. to 110° C., optionally at a temperature in the range from 55° C. to 100° C. and optionally at a temperature in the range from 60° C. to 95° C.

12. Process according to claim 1, wherein the molar ratio of the entirety of the employed compound of formula (II) to the entirety of the employed compound of formula (III) is in a range from 8:1 to 1:1, optionally in the range from 5:1 to 2:1.

13. Process according to claim 1, wherein
one of the compounds or the compound of formula (II) corresponds to formula (IIa)

$$R^1 - \overset{O}{\underset{OR^2}{\overset{\parallel}{P}}} - H \quad (IIa)$$

wherein
$R^1$ represents $(C_1-C_6)$-alkyl, $(C_1-C_6)$-haloalkyl, $(C_6-C_8)$-aryl, $(C_6-C_8)$-haloaryl, $(C_7-C_{10})$-aralkyl, $(C_7-C_{10})$-haloaralkyl, $(C_5-C_8)$-cycloalkyl or $(C_5-C_8)$-halocycloalkyl and
$R^2$ represents $(C_1-C_6)$-alkyl, $(C_1-C_6)$-haloalkyl, $(C_6-C_8)$-aryl, $(C_6-C_8)$-haloaryl, $(C_7-C_{10})$-aralkyl, $(C_7-C_{10})$-haloaralkyl, $(C_5-C_8)$-cycloalkyl or $(C_5-C_8)$-halocycloalkyl,
and
one of the compounds or the compound of formula (III) corresponds to formula (IIIa)

$$H_2C \overset{CH-CH-CN}{\underset{OAc}{\diagup}} \quad (IIIa)$$

14. Process for producing glufosinate $$H_3C - \overset{O}{\underset{OH}{\overset{\parallel}{P}}} - CH_2 - CH_2 - \overset{}{\underset{NH_2}{CH}} - \overset{O}{\overset{\parallel}{C}} - OH$$

(glufosinate)

or glufosinate salt, wherein in said process a compound of formula (Ib) is employed $$H_3C - \overset{O}{\underset{OR^2}{\overset{\parallel}{P}}} - CH_2 - CH_2 - \overset{}{\underset{O}{CH}} - CN \quad (Ib)$$
$$\underset{O}{\overset{}{\phantom{X}}} \diagdown \underset{O}{\overset{}{C}} - R^5$$

wherein $R^2$ represents $(C_1-C_{12})$-alkyl, $(C_1-C_{12})$-haloalkyl, $(C_6-C_{10})$-aryl, $(C_6-C_{10})$-haloaryl, $(C_7-C_{10})$-aralkyl, $(C_7-C_{10})$-haloaralkyl, $(C_4-C_{10})$-cycloalkyl or $(C_4-C_{10})$-halocycloalkyl, $R^5$ represents $(C_1-C_{12})$-alkyl, $(C_1-C_{12})$-haloalkyl, $(C_6-C_{10})$-aryl, $(C_6-C_{10})$-haloaryl, $(C_7-C_{10})$-aralkyl, $(C_7-C_{10})$-haloaralkyl, $(C_4-C_{10})$-cycloalkyl or $(C_4-C_{10})$-halocycloalkyl, or represents methyl and the production of the compound of formula (Ib) is effected by a process of claim 1.

15. Process for producing one or more glufosinate/glufosinate salts, optionally glufosinate, glufosinate sodium or glufosinate ammonium, comprising:
(a) producing of a compound of formula (I)/(Ib) and produced by a process of claim 1,
(b) using a compound of formula (I)/(Ib) obtained in (a) for producing glufosinate/glufosinate salts, optionally glufosinate, glufosinate sodium or glufosinate ammonium.

* * * * *